United States Patent [19]

Glazier

[11] Patent Number: 4,883,466
[45] Date of Patent: * Nov. 28, 1989

[54] NON-REUSABLE SYRINGE

[76] Inventor: Stephen C. Glazier, 211 E. 35th St., Suite 8B, New York, N.Y. 10016

[*] Notice: The portion of the term of this patent subsequent to Oct. 13, 2004 has been disclaimed.

[21] Appl. No.: 185,975

[22] Filed: Apr. 25, 1988

[51] Int. Cl.⁴ .............................................. A61M 5/00
[52] U.S. Cl. ..................................... 604/110; 604/228
[58] Field of Search ............... 604/110, 187, 218, 228, 604/111

[56] References Cited

U.S. PATENT DOCUMENTS

| | | |
|---|---|---|
| 1,712,069 | 5/1929 | Cressler . |
| 3,089,490 | 5/1963 | Goldberg . |
| 3,091,240 | 5/1963 | McConnaughey . |
| 3,380,451 | 4/1968 | Porter et al. . |
| 3,478,937 | 11/1969 | Solowey ............................. 222/386 |
| 3,577,980 | 5/1971 | Cohen . |
| 3,747,812 | 7/1973 | Karmen et al. ...................... 222/387 |
| 3,754,644 | 8/1973 | Hampel .............................. 206/63.2 |
| 3,938,513 | 2/1976 | Hargest . |
| 3,941,129 | 3/1976 | Pleznac . |
| 3,951,146 | 4/1976 | Chiquiar-Aciaz . |
| 3,998,224 | 12/1976 | Chiquar-Arias . |
| 4,252,118 | 2/1981 | Richard et al. . |
| 4,367,738 | 1/1983 | Legendre et al. . |
| 4,391,273 | 7/1983 | Chiquiar-Arias . |
| 4,439,187 | 3/1984 | Butterfield ......................... 604/111 |
| 4,449,693 | 5/1984 | Gereg ................................ 251/149.8 |
| 4,507,117 | 3/1985 | Vining et al. ....................... 604/196 |
| 4,699,614 | 10/1987 | Glazier ............................... 604/110 |

Primary Examiner—John D. Yasko
Attorney, Agent, or Firm—Harrison & Egbert

[57] ABSTRACT

An improved non-resuable syringe comprising a barrel having one open end and one restricted end through which a liquid may pass, a piston is slidably positioned within the barrel, a shaft is positioned so as to be freely slidable within the barrel and has one end extending beyond the open end of the barrel, a connector has one end engaging the piston in rotatable relation thereto, and a guide means as formed on the exterior of the shaft so as to receive the other end of the connector and causing the connector to disengage from the shaft. The piston has an orifice at one end for receiving an arrowhead-shaped portion of the connector. The connector has a forked portion having inwardly formed pins for engaging guide slots in the exterior of the shaft. The shaft includes a cylindrical member connected to the shaft and a Z-shaped groove configuration formed on opposing sides of the cylindrical member. During use of the syringe, the pins on the connector follow the pathway of the formed groove on the connector.

22 Claims, 3 Drawing Sheets

NON-REUSABLE SYRINGE

TECHNICAL FIELD

The present invention relates to syringes and, more particularly, to self-destroying or otherwise non-reusable disposable syringes.

BACKGROUND ART

Syringes are in common use today for hypodermic injection. Often these syringes are disposable syringes intended for only one use. However, these syringes are capable of repeated reuse if a user so desires. A serious problem today is that syringes are obtainable by intravenous drug addicts who repeatedly reuse and share the same syringe with other drug addicts without proper sterilization between each use. Hence, any blood-borne infectious disease that one such addict has is spread to those with whom he shares his syringes. This mechanism is thought to be a major cause of the current AIDS epidemic, as well as contributing to the spread of hepatitis, venereal disease, and other blood-borne diseases.

Recognizing this problem with the use of the injectible drugs, the present inventor has obtained U.S. Pat. No. 4,699,614, issued on Oct. 13, 1987. This patent described a non-reusable syringe having a barrel with an open end and a restricted end, a piston slidably positioned within the barrel and forming a liquid-tight seal with the interior of the barrel. A shaft is freely slidable within the barrel and extends beyond one end of the barrel. A connector engages the piston and the shaft and has a protrusion extending therefrom. A guide is formed on the shaft for receiving the protrusion of the connector. In generation, the connector is detachable from the shaft. In such invention, the connector comprises a collar holder fastened at one end of the piston, and a collar freely rotatable about the collar holder. The guide comprises a groove formed on the shaft which engages the protrusion from the connector. The guide causes the shaft to be disconnected from the piston following an injection of the liquid from the syringe.

After extensive use and experimentation with the present invention, it was found to be desirable to provide improvements to such syringe that could be manufactured and assembled less expensively, more easily, and with greater reliability. It was found that an inexpensive price of manufacture would allow the self-destructing syringes to be more widely available.

It is an object of the present invention to provide a non-reusable syringe that requires fewer parts than previous non-reusable syringes.

It is another object of the present invention to provide a non-reusable syringe that is capable of relatively simple manufacture at inexpensive prices.

It is another object of the present invention to provide a non-reusable syringe that is of inexpensive cost and is suitable for reliable widespread usage.

It is still a further object of the present invention to provide a non-reusable syringe that self-destructs following a single use, that avoids tampering, and deters the spread of fatal infectious diseases.

These and other objects and advantages of the present invention will become apparent from a reading of the attached specification and appended claims.

SUMMARY OF THE INVENTION

The present invention is a non-reusable syringe that comprises a barrel having one open end and one restricted end, a piston slidably positioned within the barrel and forming a liquid-tight seal within the interior of the barrel, a shaft freely slidable within the barrel and having one end extending beyond the barrel, a connector engaging the piston and the shaft and having two prongs extending therefrom, and two guides formed on the shaft and arranged so as to receive the prongs of the connector. The connector is detachable from the shaft. The connector is rotatably attached to the piston. The guides control the movement of the piston relative to the movement of the shaft and include means for causing the connector to detach from the shaft.

The connector is a short shaft with a arrowhead-shaped portion on one end that enters an orifice on the side of the piston facing the open end of the barrel. This connects the piston to the connector so that the connector is freely rotatable within the orifice of the piston. The shaft of the connector forks and has two prong ends at the end facing the open end of the barrel. Each of the prongs of this connector have an inwardly facing pin. Each of these pins engages one guide on the shaft. These pronged ends are manufactured to be springy such that they tend to come together at the pins when not engaged with the guides on the shaft. When sprung apart, the distance between the two prongs of the connector is greater than the outer diameter of the shaft, and the distance between the inner pins of the two prongs is less than the outer diameter of the shaft.

Each guide of the present invention comprises a groove formed in the outside surface of the shaft and arranged so as to receive a pin of the connector. The groove has a Z-shaped configuration. This groove has an open end at the end of the shaft adjacent the restricted end of the barrel. This groove has a closed end at the opposite end of this Z-shaped configuration. The groove comprises a first portion that extends from the open end linearly and longitudinally aligned with the shaft, a second portion extending at an acute angle from the end of the first portion and extending toward the end of the shaft adjacent the restricted end of the barrel, and a third portion extending at an acute angle from the end of the second portion toward the open end of the barrel. The first portion of the groove has a constant width. The second portion of the groove has a constantly increasing width between the end of the first portion and the beginning of the third portion. The third portion has a generally constant width. The third portion extends from the second portion at an angle diagonal to the axis of the shaft. This third portion has a cul-de-sac end opposite the second portion. This Z-shaped groove occurs on opposite sides of the shaft and is aligned so as to properly receive the pins formed on the prongs of the connector.

The barrel of the present invention has a generally cylindrical configuration. The restricted end of the barrel has suitable means for attaching a hypodermic needle thereto. The barrel further comprises a protrusion formed inwardly at the open end of the barrel. This protrusion defines an opening having a diameter smaller than the diameter of the shaft. This protrusion serves to restrict the further outward movement of the shaft from the barrel, once the end of the shaft adjacent to the restricted end of the barrel has approached the open end of the shaft.

DETAILED DESCRIPTION OF THE INVENTION

Figure 1:
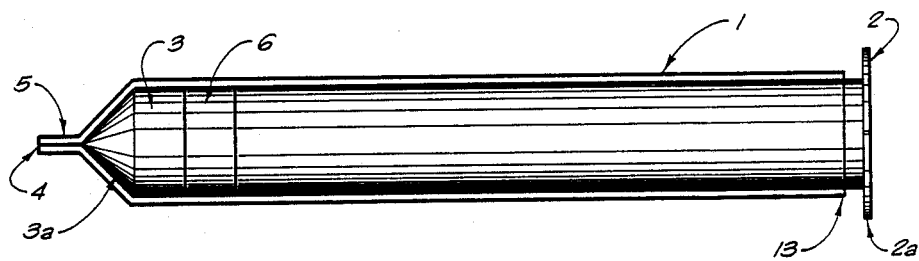
FIG. 1 is cross-sectional view, in side elevation, showing the syringe of the present invention.

Referring to FIG. 1, there is shown the improved non-reusable syringe of the present invention. In particular, FIG. 1 shows the cylindrical barrel 1, shaft 2, piston 3, restricted end 4 of barrel 1, open end 13 of barrel 1, and attachment section 5 for attaching a hypodermic needle or a tube to the syringe of the present invention. The connector system 6 of the present invention is illustrated in block form in FIG. 1.

As can be seen in FIG. 1, barrel 1 has a generally cylindrical configuration. Barrel 1 has an open end 13 through which the shaft 2 passes and a restricted end 4 through which liquid may pass. Hypodermic needles or tubes may be attached to the restricted end 4 of barrel 1.

Shaft 2 acts as the plunger of the syringe of the present invention. Shaft 2 has a generally cruciform cross-section, except for the end containing the guide means, which is a cylindrical solid. The outer diameter of shaft 2 is smaller than the general inner diameter of barrel 1. Shaft 2 is freely slidable within barrel 1. As can be seen in FIG. 1, shaft 2 has a circular end cap 2a at the end of shaft 2 exterior of barrel 1.

Piston 3 is slidably positioned within the interior of barrel 1. Piston 3 forms a liquid-tight seal within the interior of the barrel. Piston 3 has an outer diameter slightly smaller than the inside diameter of barrel 1. This piston 3 is slidable from one end of the barrel 1 to the other end. As will be described hereinafter, piston 3 has a generally open interior area and an orifice through which the one portion of the connector of the present invention may be inserted. In assembly, piston 3 is inserted through the open end of barrel 1. Piston 3 has an end face 3a that is adjacent the restricted end 4 of barrel 1. End face 3a has a surface shape that exactly matches the surface shape of the inside surface of the restricted end 4 of barrel 1.

Figure 2:
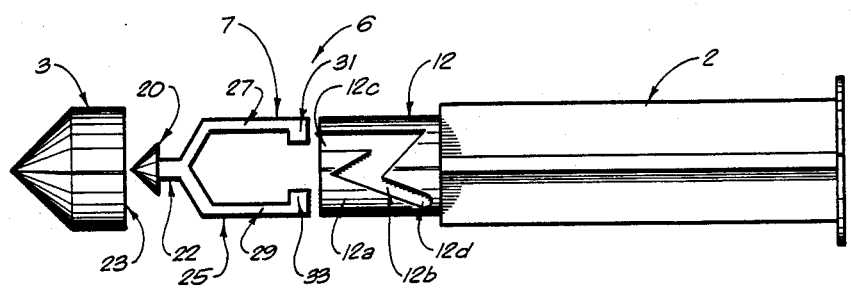
FIG. 2 is an exploded view of the present view of the present invention isolating the connector and guide system.

FIG. 2 shows a more detailed view of the connector system 7 and the guide system 12 of the present invention. In operation, the connector system 7 engages the interior of piston 3. In particular, the connector system 7 has a first end 20 that is inserted into the orifice of piston 3 and is freely rotatable within this interior portion. It is an important aspect of the present invention that the connector 7 be freely rotatable relative to the piston 3. The first end 20 of connector 7 has an arrowhead shape that permits ease of insertion into the orifice of the piston. The 'arrowhead' shape allows the end 20 to be inserted but makes removal from the orifice difficult. In practice, the attempted removal of the end 20 from the orifice of piston 3 will result in destruction, deterioration, or damage to the orifice such that reuse of the assembly of the present invention would be difficult. The first linear portion 22 extends outward from this first end 20. Following assembly, first linear portion 22 will extend outwardly beyond the back face 23 of piston 3. A forked member 25 extends outwardly from the end of first linear member 22 opposite first end 20. Forked member 25 includes a first prong 27 and a second prong 29. The first prong 27 extends in one direction outwardly from the first linear member 22. This first prong 27 has an inwardly extending pin 31 formed at the end of the prong 27 opposite the first linear member 22. The second prong 29 also extends outwardly from the end of first linear member 22 in another direction. Second prong 29 also has an inwardly extending pin 33 at its end opposite the linear member 22. Pins 31 and 33 will each engage a groove 12b on opposite sides of guide system 12.

Figure 5:
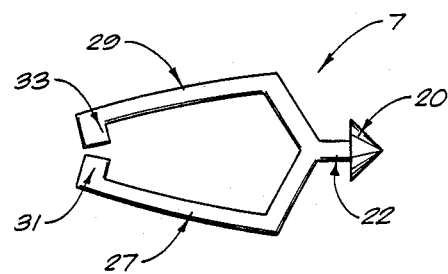
FIG. 5 is a detailed view showing the connector of the present invention prior to assembly with the syringe of the present invention.

FIG. 5 shows the configuration of connector 7 prior to assembly. Importantly, it can be seen that the prongs 27 and 29 are manufactured so as to be somewhat springy. Following manufacture, as illustrated in FIG. 5, the prongs 27 and 29 tend to come together at the ends 31 and 33. This allows the closing of the prongs following the initial use of the syringe 1 of the present invention and the connector 7 detaches from the guides 12. When the prongs 27 and 29 return to the position shown in FIG. 5, following use of this syringe, it becomes difficult or impossible to cause these pins 31 and 33 to be reinserted into the guide system 12 with the piston 3 and connector 7 remaining in barrel 1. Reassembly becomes additionally difficult because of the free rotation between the connector 7 and the piston.

FIG. 2 also shows the guide system 12 of the present invention. The guide system 12 of the present invention is formed on the exterior of shaft 2. Essentially, a solid cylindrical member 12a is formed at the end of shaft 2 nearest the restricted end 4 of barrel 1. In terms of the manufacturing process, solid cylindrical member 12a and shaft 2 are of unitary configuration. Importantly, however, this should not be considered a limitation of the present invention. It is also possible to manufacture the cylindrical member 12a and the shaft 2 separately and, thereafter, attach them together properly. The diameter of cylindrical member 12 will be less than the inner diameter of the barrel 1 of the syringe of the present invention.

Guide system 12 includes a groove 12b that is formed on the exterior of cylindrical member 12a. In the preferred embodiment of the present invention, there are two grooves formed on the cylindrical member 12a and are located approximately 180 degrees from each other. The first groove 12b is formed on the cylindrical member for receiving one of the pins 31 or 33 of the connector 7 and a second groove is formed (not shown) on the opposite side of the cylindrical member 12a for receiving the other of the pin 31 or 33 of connector 7. These grooves 12b are aligned with one another so as to allow the pins 31 and 33 to slide freely therethrough. Each of the grooves 12b should be of the same shape as the other groove. The minimum width of each of the grooves 12b is slightly greater than the width of the pins 31 or 33.

Each groove is a modified Z-shape. Each groove 12b has an open end 12c at the end of the shaft 2 adjacent the restricted end 4 of barrel 1. The groove has a closed end 12d at the opposite end of the Z-shaped configuration. These grooves 12b are arranged such that the prongs 27 and 29 may be aligned so as to match the opening of the groove.

Figure 3:
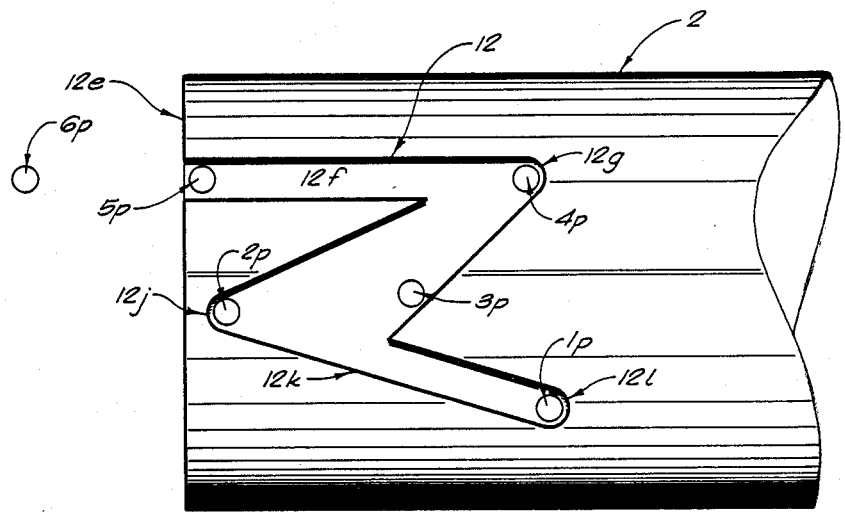
FIG. 3 is a close-up view of the guide system of the present invention.

The shape of the groove 12b is more specifically shown in FIG. 3. The groove 12b begins at the end 12c of shaft 2. As can be seen, groove 12b opens at the end 12c. Groove 12b then forms a first portion 12f that travels straight back extending linearly from open end 12e and is longitudinally aligned with the shaft 2. First portion 12f has a generally constant width and extends to an acute angle corner 12g in the groove 12b. At the acute angle corner 12g, a second portion 12h of groove 12b is formed. This second portion 12h extends at an acute angle from the end 12g of first portion 12f and extends toward the end of shaft 2 adjacent the restricted end of barrel 1. This second portion 12h extends at an acute angle corner 12j. End 12j does not open at the end 12e, but is a closed corner. A third portion 12k extends from corner 12j at the end of the second portion 12h and extends toward the open end of barrel 1. This third portion 12k extends from the second portion 12h at an angle diagonal to the axis of shaft 12. This third portion 12k has a cul-de-sac end 12l opposite corner 12j. In terms of shape, the first portion 12f of groove 12b has generally constant width. The second portion 12h of groove 12b has a constantly increasing width between the end 12g of first portion 12f and the end 12j of third portion 12k. Third portion 12k has generally constant width.

It is through groove 12b that the pins 31 and 33 of prongs 27 and 29 respectively, of connector 7 pass.

As shown in FIG. 3, the various positions of the pins 31 or 33 within groove 12b are shown. Initially, the syringe is delivered to the user such that the pins are in position 1. In position 1, the shaft may be compressed against the pins so as to push the piston 3 against the restrictive end of barrel 4, as in the assembly of the present invention. After the shaft 2 is compressed against the restricted end 4 of barrel 1, the shaft must be pulled outwardly through the barrel 1. This will serve to draw fluid into the hypodermic needle and through the restricted end 4 of barrel 1. In pulling out the shaft to draw the fluid into the barrel 1, the pins will move from position 1 to position 2 through groove 12k and to corner 12j. The pins 31 will abut corner 12j such that the outward movement of shaft 2 will cause piston 3 to be moved through the barrel 1 away from the restricted end 4. After fluid has been drawn into barrel 1, it will be necessary to compress the shaft 2 so as to deliver the fluid to the patient. When the shaft 2 is compressed, pin 31 will move from position 2 to position 3. At position 3, the pin 31 will abut the wall of groove 12h. Pin 31 will then travel along the side of groove 12h until it reaches position 4 at corner 12g. At position 4, the compression of the shaft 2 will cause the piston 3 to move toward the restricted end 4 of barrel 1. It is this action that delivers the medication to the patient.

At this stage of the use of the syringe of the present invention, the pins 31 and 33 remain at position 4 and the piston 3 abuts the restricted end 4 of barrel 1. If a person desires to reuse the syringe following this step, it would be vitally necessary to be able to draw fluids again into barrel 1 by pulling shaft 2 outwardly from barrel 1. Such a movement would cause the pin 31 to move from corner 12g (and position 4) through groove 12f. Ultimately, the pins 31 and 33 would exit the groove 12b by passing to position 5 and position 6. At all times during this second draw, the piston 3 will remain in abutment with the restricted end 4 of barrel 1.

Since the pins 31 and 33 would not abut another surface, the piston could not be drawn away from the restricted end 4.

When the pins 31 and 33 are in position 6, the pins 31 and 33, and the associated connector 7, are disconnected from the shaft 2. This disconnects the shaft 2 from the piston 3 such that the shaft 2 may be pulled of towards the open end of the barrel 1 without causing the piston 3 to move toward the open end 13 of barrel 1. Although the shaft 2 may be recompressed into barrel 1, it may only further push the piston 3 toward the restricted end 4 of barrel 1. It would not cause the piston 3 to move toward the open end 13 of barrel 1. The connector 7 cannot be re-engaged with guides 12 because the tips 31 and 33 of prongs 27 and 29 have sprung together. This syringe is thus rendered unable to be filled with a second load of fluid for a second injection and thus is rendered non-reusable after it is filled and emptied once and only once.

Figure 4:
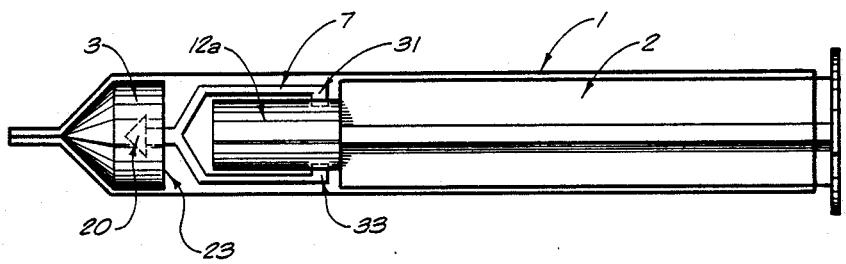
FIG. 4 is a cross-sectional view of the syringe as assembled prior to use.

The rotatable relationship between the connector 7 and the piston 3 is shown in FIG. 4. It can be seen that the arrowhead-shaped end 20 is inserted into the interior of piston 3. The shape of end 20 prohibits its removal from the end 23 of piston 3. it should be noted that pistons used in current syringes generally have an open interior area. This 'free' type of engagement between the end 20 and the interior of piston 3 allows free rotation of the connector 7 with respect to the piston 3. As such, when the connector 7 and the associated pins 31 and 33 are moved to position 6 (shown in FIG. 3), the rotation of the connector 7 will make it difficult or impossible for the pins 31 and 33 to retrace their path in the grooves 12b back to position 1. Additionally, following the use of this syringe, the connector 7 will reform into a shape illustrated in FIG. 5. The internal closing of the prongs following use, will also make it difficult or impossible for the connector 7 to retrace its path through the guide system 12.

Figure 6:
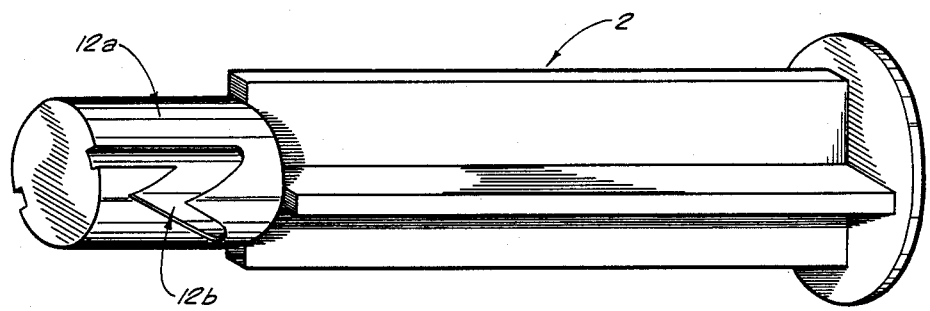
FIG. 6 is an isolated view, in perspective, of the shaft/guide system configuration of the present invention.

FIG. 6 illustrates the configuration of the shaft 2 of the present invention. Following experimentation with a prior-art patent, by the same inventor, it was found that the manufacturing cost of shaft 2 would be significantly less than other non-reusable syringe manufacturing techniques. Importantly, cylindrical member 12a is a solid member. No internal forms or manipulators are required in order to create internal grooves or a cylindrical cavity. In the process of plastic molding, it is a rather simple procedure to mold the Z-shaped groove 12b on a solid cylindrical member 12a. This can be done during the formation of the shaft 2.

The present invention is a non-reusable improvement over present syringes. Importantly, the non-reusable feature of the present invention can be accomplished by the utilization of a single additional component, the connector 7. As such, the non-reusable syringe of the present invention can be manufactured by the molding of the shaft 2 by including the solid cylindrical portion 12a with inscribed groove 12b. In a manufacturing sense, connector 7 is a simple moldable element. The piston 3, as described in the present invention, is a standard piston used on conventional syringes. Because of the simplicity of manufacture, the present invention offers a 'non-reusable' alternative to present day syringes.

The present invention provides a safe and automatically self-destroying syringe. Since the syringe of the present invention can only be used one time, it serves to deter the spread of fatal infectious diseases and to deter the theft and abuse of controlled substances. The present invention eliminates the possibility of sharing and reusing a contaminated syringe. The configuration of the present invention offers a cost-effective alternative to present syringes and offers a technique that is easy to manufacture and easy to implement. No additional instruction will be required to enable a physician, or allied health care professional, to properly use the present invention.

The embodiments as illustrated and discussed in this specification are intended only to teach those skilled in the art the best way known by the inventor to make and use the invention. Nothing in the specification should be considered as limiting the scope of the present invention. Many changes could be made by those skilled in the art to produce equivalent systems without departing from the invention. The present invention should only be limited by the following claims and their legal equivalents.

I claim:

1. An improved non-reusable syringe comprising:
    a barrel having one open end and one restricted end through which a fluid may pass;
    a piston slidably positioned within said barrel, said piston forming a liquid-tight seal with the interior of said barrel;
    a shaft slidable within said barrel, said shaft extending beyond one end of said barrel;
    connector means having one end engaging said piston such that said connector means is rotatable relative to said piston; and
    guide means formed on said shaft, said guide means receiving the other end of said connector means, said guide means for controlling the movement of said piston relative to the movement of said shaft, said guide means causing said connector means to disengage from said shaft.

2. The syringe of claim 1, said piston having an orifice at the end opposite the restricted end of said barrel, said orifice for receiving one end of said connector means.

3. The syringe of claim 2, said connector means comprising:
    a first end rotatably received by said orifice of said piston; and
    a second end having a pin formed thereon, said pin slidably engaging said guide means.

4. The syringe of claim 3, said pin fitted within said guide means for tracking the path of said guide means, said guide means formed on the exterior of said shaft, said pin extending inwardly of said connector means.

5. The syringe of claim 3, said second end of said connector means being forked into a first and second prong, each of said first and second prongs having an inwardly extending pin for engaging said guide means.

6. The syringe of claim 1, said guide means comprising:
    a cylindrical member connected at the end of said shaft adjacent said restricted end of said barrel; and
    a groove formed on the surface of said cylindrical member, said groove for receiving the other end of said connector means, said connector means slidable within said groove.

7. The syringe of claim 6, said groove having a Z-shaped configuration, said groove having an open end at the end of said shaft adjacent said restricted end of said barrel, said groove having a closed end at the opposite end of said Z-shaped configuration.

8. The syringe of claim 7, said groove comprising:
    a first portion extending from said open end linearly and longitudinally aligned with said shaft;
    a second portion extending at an acute angle from the end of said first portion and extending toward the end of said shaft adjacent said restricted end of said barrel; and
    a third portion extending at an acute angle from the end of said second portion and toward said open end of said barrel.

9. The syringe of claim 8, said first portion of said groove having a constant width, said second portion of said groove having a constantly increasing width between the end of said first portion and the beginning of said third portion, said third portion having a generally constant width.

10. The syringe of claim 8, said third portion extending from said second portion at an angle diagonal to the axis of said shaft, said third portion having a cul-de-sac end opposite said second portion.

11. The syringe of claim 6, said cylindrical member being solid, said groove formed on the exterior surface of said cylindrical member, said cylindrical member integrally formed with said shaft.

12. The syringe of claim 1, said barrel comprising:
    a protrusion formed inwardly at said open end of said barrel, said protrusion restricting the travel of said guide means to within said barrel.

13. A connector for the releasable connection between the piston of a syringe and a shaft of a syringe, said shaft having a guide area formed thereon, said connector comprising:
    a first end having a configuration suitable for rotatable connection to said piston;
    a linear portion extending outwardly from said first end; and
    a forked member extending outwardly from the end of said linear portion opposite said first end, the opposite ends of said forked member having pins for slidable engagement with the guide areas of said shaft.

14. The connector of claim 13, said first end having an arrowhead shape for non-removable insertion into the orifice of said piston.

15. The connector of claim 13, said first end, said linear portion, and said forked member being integral.

16. The connector of claim 13, said forked member comprising:
    a first prong extending in one direction from said linear portion, said first prong having an inwardly extending pin at the end opposite said linear portion; and
    a second prong extending outwardly in the other direction from said linear portion, said second prong having an inwardly extending pin at the end opposite said linear portion, said first and second prongs for engaging said guide areas on opposite sides of said shaft.

17. An improved non-reusable syringe comprising:
    a barrel having an open end and a restricted end through which a liquid may pass;
    a piston slidably positioned within said barrel, said piston forming a liquid-tight seal with the interior of said barrel;
    a shaft slidable within said barrel, said shaft extending beyond one end of said barrel;
    a connector having one end engaging said piston such that said piston moves relative to the longitudinal movement of said connector within said barrel; and guide means formed on the exterior of said shaft, and guide means slidably receiving said connector, said guide means for controlling the movement of said piston relative to the movement of said shaft, said guide means causing said connector to disengage from said shaft.

18. The syringe of claim 17, said piston rotatably receiving said one end of said piston.

19. The syringe of claim 17, said guide member comprising a solid cylindrical member connected to the end of said shaft, said cylindrical member having a first groove formed on the exterior surface, said first groove receiving the other end of said connector, said connector slidable within said first groove.

20. The syringe of claim 19, said cylindrical member having a second groove formed approximately 180 degrees removed from said first groove, said second groove receiving another portion of the other end of said connector.

21. The syringe of claim 20, said connector comprising:
a first end rotatably connected to said piston such that said connector rotates about the longitudinal axis of said connector during travel through said first and second grooves; and
a forked member having first and second prongs extending outwardly from said first end, said first and second prongs having inwardly extending pins engaging said first and second grooves in said cylindrical member.

22. The syringe of claim 17, said barrel comprising:
a protrusion formed inwardly at said open end of said barrel, said protrusion restricting the travel of said guide means to within said barrel.

* * * * *